United States Patent [19]

Madaus et al.

[11] Patent Number: 4,820,870
[45] Date of Patent: Apr. 11, 1989

[54] ACIDIC ALKALI CITRATE AND COMPOSITIONS FOR ADJUSTING THE PH OF URINE

[75] Inventors: Rolf Madaus, Köln-Brück; Werner Stumpf; Klaus Görler, both of Bensberg-Refrath, all of Fed. Rep. of Germany; Alfonso Carcasona-Beltran, Barcelona, Spain

[73] Assignee: Dr. Madaus & Co., Ostmerheimer Str., Fed. Rep. of Germany

[21] Appl. No.: 33,916

[22] Filed: Apr. 1, 1987

Related U.S. Application Data

[60] Continuation of Ser. No. 852,093, Apr. 14, 1986, abandoned, which is a continuation of Ser. No. 692,323, Jan. 16, 1985, abandoned, which is a continuation of Ser. No. 469,493, Feb. 24, 1983, abandoned, which is a division of Ser. No. 223,646, Jan. 9, 1981, Pat. No. 4,400,535, which is a continuation of Ser. No. 112,994, Jan. 17, 1980, abandoned, which is a continuation of Ser. No. 916,373, Jun. 16, 1978, abandoned.

[30] Foreign Application Priority Data

Jun. 16, 1977 [DE] Fed. Rep. of Germany ....... 2727304

[51] Int. Cl.$^4$ ............................................. C07C 59/265
[52] U.S. Cl. .................................................... 562/584
[58] Field of Search ......................... 562/584; 514/574

[56] References Cited

U.S. PATENT DOCUMENTS 3,658,969 4/1972 Renie .................................. 514/574

OTHER PUBLICATIONS

*Hackh's Chemical Dictionary*, 4th Ed. (1969) at page 161, McGraw-Hill, Publ.

*Primary Examiner*—Paul J. Killos
*Attorney, Agent, or Firm*—Felfe & Lynch

[57] ABSTRACT

The invention provides a novel acidic alkali citrate having the formula $K_6Na_6H_3(C_6O_7H_5)_5 \cdot 2\text{-}4\ H_2O$ made by dissolving either (a) trisodium citrate$\times 2\ H_2O$, tripotassium citrate$\times 1\ H_2O$, and citric acid in a mole ratio of 2:2:1 in 3 to 5 times the quantity by weight of boiling demineralized water, based on the weight of the citric acid and maintaining the solution at a temperature not lower than 60° C.; or (b) citric acid at 90° C. while stirring in .01 to 1 times its weight of demineralized water and then adding sodium carbonate and potassium carbonate to give a mole ratio of 3:3:5 of sodium carbonate: potassium carbonate:citric acid, and quick drying the homogeneous solution obtained. Therapeutic agents for the treatment of urolithiasis and removal, or preventing recurrence, of urine stones comprising said acidic alkali citrate are provided.

3 Claims, No Drawings

ACIDIC ALKALI CITRATE AND COMPOSITIONS FOR ADJUSTING THE PH OF URINE

This application is a continuation of application Ser. No. 852,093, filed Apr. 14, 1986, now abandoned; which is a continuation of application Ser. No. 692,323, filed Jan. 16, 1985, now abandoned; which is a continuation of application Ser. No. 469,493, filed Feb. 24, 1983, now abandoned; which is a division of application Ser. No. 223,646, filed Jan. 9, 1981, which is now U.S. Pat. No. 4,400,535; which is a continuation of application 712,994, filed Jan. 17, 1980, now abandoned; which is a continuation of application Ser. No. 916,373, filed June 16, 1978, now abandoned.

The invention relates to an acidic alkali citrate and to urine pH adjusting compositions containing same. In further aspect, the invention provides a process for the preparation of such citrate.

Uric acid develops in the human organism as a final product of the purine metabolism. Dependent on the pH-value of the urine, a displacement of the highly soluble urate salts may occur in favor of the less soluble salts or undissociated uric acid. The solubility increases again at pH-values of more than 6 and at physiological concentrations, and at this pH precipitated uric acid already tends to enter again into solution. For the treatment of patients suffering from uroliths, agents which increase the uric pH-value are therefore administered. The classic method of such a treatment is the administration of lemon juice (B. Bibus, Wien. Med. Wschr. 118, 416 (1968)). This method, has, however, the disadvantage of potentially inaccurate dosing as well as gastric incompatibility. A controlled increase of the uric pH-value vas sought to be reached years ago by administration of an alkali-citric acid-mixture in a syrup-like solution (H. Eisenberg et al, J. Clin. Endocrin. 15, 503 (1955)), or also of dry mixtures of sodium citrate, potassium citrate, and citric acid (Der Urologe, 4, 156, (1965)).

Such a syrup-like solution must, however, be fresly prepared before use. Moreover, it contains sugar (diabetes-contra-indication). The proposed dry mixtures known until now lead in the course of time to a lumpy mixture caused by topochemical reactions, and are thus not satisfactory. It has also been proposed to use dry preparations containing citrate in granulated form or as tablets containing ion sources other than citrate. These preparations, too, however, were found not to be stable.

Therefore, there has been a need for a stable and storable product to produce a pH-value in urine of between 0.2 and 7.0 after setting free the citrate-, sodium-, and potassium ions in an exactly defined proportion corresponding to the predetermined dosage. pH-values below 6.2 are insufficient for lithotriptic treatment; values higher than 7.0 pose the danger of phosphate-coat formation around the urolith, preventing the dissolution of the stone. The above pH-values must therefore be adhered to exactly for successful therapy.

Surprisingly, it has been found when producing a concentrated aqueous alkaline hydrogen citrate solution that anomalies arise which are thought to be due to complex formation by these salts in solutions: deviations are observed between the calculated values and the experimentally obtained value of the mobility and activity of the sodium ions, when determining their electrochemical potentials. When measuring nuclear spin resonance, results pointing also to complex formation in sodium-citrate solutions are obtained.

It has now been found that stable, homogeneous and storable products can be obtained by suddenly cooling high ion concentration solutions; these products have desirable uric pH-value influence properties and activities.

It is therefore the objective of the invention to provide a solid product which is stable and indefinitely storable which releases citrate-, sodium-, and potassium ions in certain equivalent proportions when used as a therapeutic agent, producing, at the proper dosage, a therapeutically desired pH increase of the urine to pH 6.2–7.0. The product of the invention has a good compatibility, allows simple dosing, and dissolves uroliths as well as preventing their recurrence. The individual components for making the inventive agents, viz., sodium carbonate, potassium carbonate and/or sodium hydroxide (or potassium hydroxide and citric acid) react in a mole ratio of 3:3:5 in the case of carbonates and 6:6:5 (in the case of hydroxides), in aqueous solution. The reaction may preferably also take place in solutions of trisodium citrate $\times 2H_2O$, tripotassium citrate $\times 1H_2O$, and citric acid in a mole ratio of 2:2:1. These initial components are surprisingly not detectable in the final product. The obtained acidic alkali citrate rather exists in the condition of a defined crystalline product of the formula $K_6Na_6H_3(C_6O_7H_5)_5 \cdot 2\text{-}4H_2O$. Administration of the product according to the invention to patients with hyperuricuria (increase of uric acid in the urine) permits facile control of the dosage and, thus, effects an exact therapeutic pH-increase of the urine.

Administration of the invention composition dissolves uroliths and prevents their recurrence. Since the inventive agent is free of carbohydrates it has special advantages for diabetics who represent a large part of uric acid patients. The pH-regulating effect is reached with comparatively low dosages, for example, 10 g/day. A medication over a period of years is possible because of the good compatibility of the compound.

A further aspect of the invention is a process for obtaining the acidic alkali citrate of the formula $K_6Na_6H_3(C_6O_7H_5)_5 \cdot 2\text{-}4H_2O$. Essentially, the process of the invention comprises dissolving trisodium citrate $\times 2\ H_2O$, tripotassium citrate $\times 1H_2O$ and citric acid in a mole ratio of 2:2:1 in 3 to 5 times, especially 3.7 times, the quantity by weight of boiling water relative to the weight of citric acid dissolved. The temperature of the solution is not allowed to be below 60° C., and the homogeneous solution is subjected to quick drying.

The process can also be effected by dissolving citric acid in 0.5 to 1.0 times, especially 0.63 times, its quantity by weight of demineralized water at 90° C. while stirring, and then adding sodium carbonate and potassium carbonate in solid form at a mole ratio of citric acid:potassium carbonate:sodium carbonate of 5:3:3. The hot solution is then worked up as described above.

When using NaOH and KOH, or $NaHCO_3$ and $KHCO_3$, the mole ratio needs to be adjusted accordingly.

A reverse sequence of addition is possible, i.e., firstly adding alkali carbonate and then citric acid. The water hydration content is adjusted to be approximately 2–5%.

Pharmacological and clinical testing of the agent according to the invention lead to the following observations which indicate a certain mechanism of action:

In body cells citric acid is oxidized to 6CO$_2$ and 6H$_2$O. A person of 70 kg of weight can oxidatively convert approximately 200 mMoles of citrate per hour. Metabolically, 1 mole of the acidic alkali citrate according to the invention gives 5 moles of citric acid which are quantitatively metabolized into CO$_2$ and H$_2$O. At the same time 12 mole of OH ions are developed which are available for acid neutralization. For example:

$$K_6Ha_6H_3(C_6O_7H_5)_5 \times 3H_2O + 3H_2O = 5(C_6O_7H_8) + 6K^+ + 6Ha^+ + 12OH^-$$

This indicates that 2.5 g of the acidic alkali citrate according to the invention administered orally causes lowering, by 22 mMoles of H$^+$ ion elimination. As the pH of urine is influenced by the phosphate buffer mixture, and the body eliminates approximately 30 mMoles of phosphate ions per day, 30 mMoles of H$^+$ ions are conserved when changing from H$_2$PO$_4^-$ to HPO$_4^=$. Thereby the pH-value would already be increased from 4.8 to approximately 6.5. If HPO$_4^=$ ions were changed still further, to PO$_4^=$, another 30 mMoles would be conserved, and the pH-value would be higher than 7.0. These values are registered by the titration acidity of the urine of approximately 30–50 mMoles a day. In order to reach an effective neutralization of the urine one must therefore employ at least 5.0 g of the acidic alkali citrate. But since from pH 6.0 on the tubules of the kidney react with an increased elimination of citrate and CHO$_3^-$ whereby the H$^+$ ions are bound, and the secretion of NH$_4^+$ ions is decreased by approximately 30–50 mMoles, in fact double that dosage is necessary. Thus, about 10 g of the inventive acidic alkali citrate corresponds to the usual dosage in practice. The necessary dosage may be lower as PO$_4^=$ elimination decreases and raised when the PO$_4^=$ elimination is greater. By adding the mMoles of titration acidity (A) and mMoles of NH$_4^+$ in urine over 24 hours, the necessary dosage of alkali citrate can individually be prescribed. For the inventive acidic alkali citrate the following formula can be used:

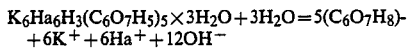

$$\frac{\text{mMole } A/24 \text{ hours} + \text{mMole NH}_4^+/24 \text{ hours}}{9} = \text{g compound/day}$$

(wherein "compound" is the inventive acidic alkali citrate). In the use of the new compound against uroliths and in uric acid diathesis the urine pH-value of the patients is controlled. The patient can do this himself using indicator paper and keeping a control calender. The compound is dosed to produce the desired effect, i.e., the pH-value must be determined before each administration and the dosage determined therefrom. The average daily dosage is 10 g and should be ingested, preferably together with a liquid, gradually during the day. Preferred are 2.5 g in the morning, 2.5 g at noon, and 5.0 g in the evening. In any case the individual dosage is to be determined to bring the pH-value of urine into the optimal range of between 6.2 and 7.0.

The following conditions are determining factors for the diagnosis: typical complaints (colics) and haematuria, proof of uric acid crystals in the sediment (brick dust deposit), analysis of the passed concrement, constant urine pH-values below 5.5, uric acid in serum of more than 5.5 mg/100 ml in men and more than 4.3 mg/100 ml in women, indication of the existence of stones by X-rays, by brightening or recess in the excretion urogram or a retrograde pyelogram. The inventive acidic alkali citrate K$_6$Na$_6$H$_3$(C$_6$O$_7$H$_5$)$_5 \times$2–4H$_2$O should be the therapy of choice for uroliths, uric acid diathesis, and general stone formation proclivity. Past clinical tests show a success rate of 95%. The treatment is not effective in only very few special cases. These are mostly strong shade throwing concrements (mixed stones) and uncontrolled infections of the urinary passages. The only danger in administration of the inventive agent is a hyperalkalinity due to wrong and excessive dosing over a long time leading to exceeding the upper limit of the pH-value of 7.0; as a result of this, phosphate stones may develop. When adjusting the urinary pH-values to 6.2 to 7.0 the following clinical results were found:

(1) disappearance of the subjective complaints (feeling of pressure and tension in the renal region, typical colics), (2) inhibited microhaematuria, (3) brick dust desposit no longer demonstrable (4) X-ray control shows a diminution or a break-up of the concrement.

The necessary duration of the treatment depends on the position, form, size and age of the stone. The lithotriptic effect is obviously better, the greater the quantity of urine which surrounds the stone.

EXAMPLE 1

194.4 kg of tripotassium citrate×1H$_2$O, 176.4 kg trisodium citrate×2H$_2$O, and 57.6 kg citric acid were dissolved in 210.0 l of boiling demineralized water. The temperature of the solution was then lowered to about 70°–80° C., taking care that no particles precipitate. Thereafter the homogeneous solution was transferred continuously onto a two-roller-drier by means of a pump and was rapidly dried. The layer thickness on the rollers was 0.5 to 0.8 mm. The dry rollers were operated with saturated steam of 5–7 excess atmosphere of pressure so that a temperature of 140°–160° C. of the roller surface resulted. By adjusting the rotation speed, the product was made to stay on the roller for about 5 seconds. The output is 30–35 kg of dry product per m$^2$ heating surface and hour. The cylinders of the rollers were of fine grained special gray cast iron with perlitic constitution, turned outside and inside, ground and strongly hard-chrome plated. The residual final drying was effected on plate driers to about 3% H$_2$O.

The product was characterized as K$_6$Na$_6$H$_3$(C$_6$O$_7$H$_5$)$_5$.2–4H$_2$O based on analytical data set forth below and its spectroscopic data shown in:

FIG. 1 which is an X-ray diagram (goniometric picture of the X-ray diffraction spectrum) of the product; and FIG. 2 which is a Raman-spectrum of the product.

X-ray diagram (goniometric picture of the X-ray diffraction spectrum)

(see FIG. 1)

Raman spectrum (see FIG. 2)

| | Analytical composition: | |
|---|---|---|
| | found: | theoretical: |
| Potassium: | 17.40% | 17.76% |
| Sodium: | 10.42% | 10.44% |
| Citrate: (total) | 71.77% | 71.57% |

(all values refer to the anhydrous substance)

EXAMPLE 2

1,050.50 kg of citric acid were suspended while stirring in 675 l of demineralized water at about 90° C. (a part of the citric acid did not dissolve initially. Then 317.97 kg of sodium carbonate (anhydrous) in solid form and 414.63 kg of potassium carbonate (anhydrous) were added while stirring and maintaining the above temperature. On completion of the reaction no more $CO_2$ was evolved and all substances were in solution. The solution was worked up as in Example 1. The product obtained had the same elementary analysis and X-ray diffraction spectrum as that of Example 1.

EXAMPLE 3

317.97 kg of sodium carbonate (anhydrous) and 414.63 kg of potassium carbonate (anhydrous) were suspended while stirring in 675 l of water at 90° C. Then 1,050.50 kg of citric acid in solid form were slowly added, while keeping the above temperature and stirring, until the reaction was finished. No more $CO_2$ was separated. Thereafter the process was continued as described in Example 1.

We claim:

1. Acidic alkali citrate of the formula $$K_6Na_6H_3(C_6O_7H_5)_5.2-4H_2O.$$

2. Therapeutic agent for increasing the pH of urine comprising a therapeutically effective amount of an acidic alkali citrate as claimed in claim 1 in a pharmaceutically acceptable excipient.

3. Method for treating urolithiasis which method comprises administering to an afflicted subject a therapeutically effective amount of an acidic alkali citrate as claimed in claim 1 in a pharmaceutically acceptable excipient.

* * * * *